United States Patent [19]

Bruno

[11] Patent Number: 5,209,738
[45] Date of Patent: May 11, 1993

[54] METHOD AND APPARATUS FOR ENABLING SAFE RECAPPING OF HYPODERMIC NEEDLES

[76] Inventor: John Bruno, 77-83 Second Ave., Paterson, N.J. 33431

[21] Appl. No.: 849,995

[22] Filed: Mar. 10, 1992

Related U.S. Application Data

[63] Continuation of Ser. No. 546,181, Jun. 28, 1990, abandoned.

[51] Int. Cl.⁵ .............................................. A61M 5/32
[52] U.S. Cl. ................................... 604/192; 604/263; 206/366
[58] Field of Search .................. 206/364–366; 248/154, 683; 604/263, 192, 110, 187

[56] References Cited

U.S. PATENT DOCUMENTS

| | | | |
|---|---|---|---|
| 2,194,997 | 3/1940 | Butler | 248/683 |
| 3,288,420 | 11/1966 | Marouka | 248/683 |
| 4,742,910 | 5/1988 | Staebler | 604/192 |
| 4,804,090 | 2/1989 | Schuh et al. | 206/366 |
| 4,915,698 | 4/1990 | Levenson | 604/263 |

FOREIGN PATENT DOCUMENTS 2198644 6/1988 United Kingdom ............... 604/192

*Primary Examiner*—C. Fred Rosenbaum
*Assistant Examiner*—Ronald K. Stright, Jr.
*Attorney, Agent, or Firm*—Morgan & Finnegan

[57] ABSTRACT

A method and device for recapping hypodermic needles or syringes with a one-handed operation. The device includes a housing with an open end and ballast material located at the bottom of the housing. A resilient sheath gripper is provided within said housing for gripping the needle sheath in an upright position. A sheath engaging surface is also provided to engage the needle tip during the recapping operation. The sheath gripper can be configured by folding a resilient strip about a plurality of clips to form a resilient sheath gripping opening. The device can incorporate a holder for releasably supporting the recapping device in an upright position; a suction device for secure mounting to a supporting surface; and adhesive devices for mounting the recapping device to non-horizontal surfaces. The quantity of ballast may be configured to be adjustable as desired. The housing can also be formed in decorative manners.

30 Claims, 4 Drawing Sheets

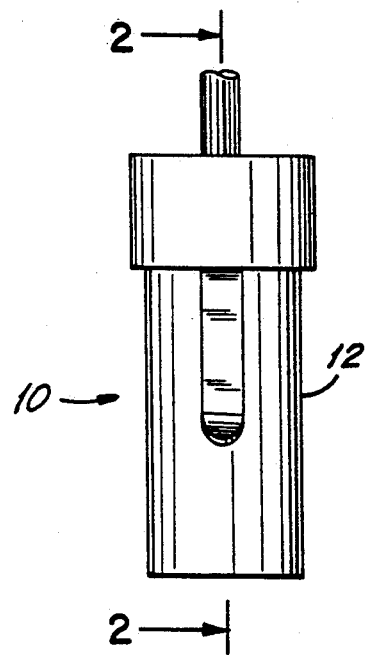
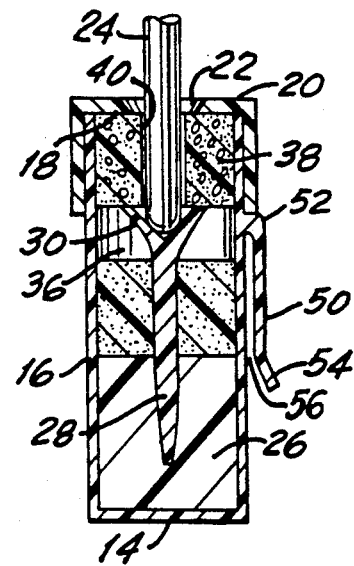
FIG. 1   FIG. 2
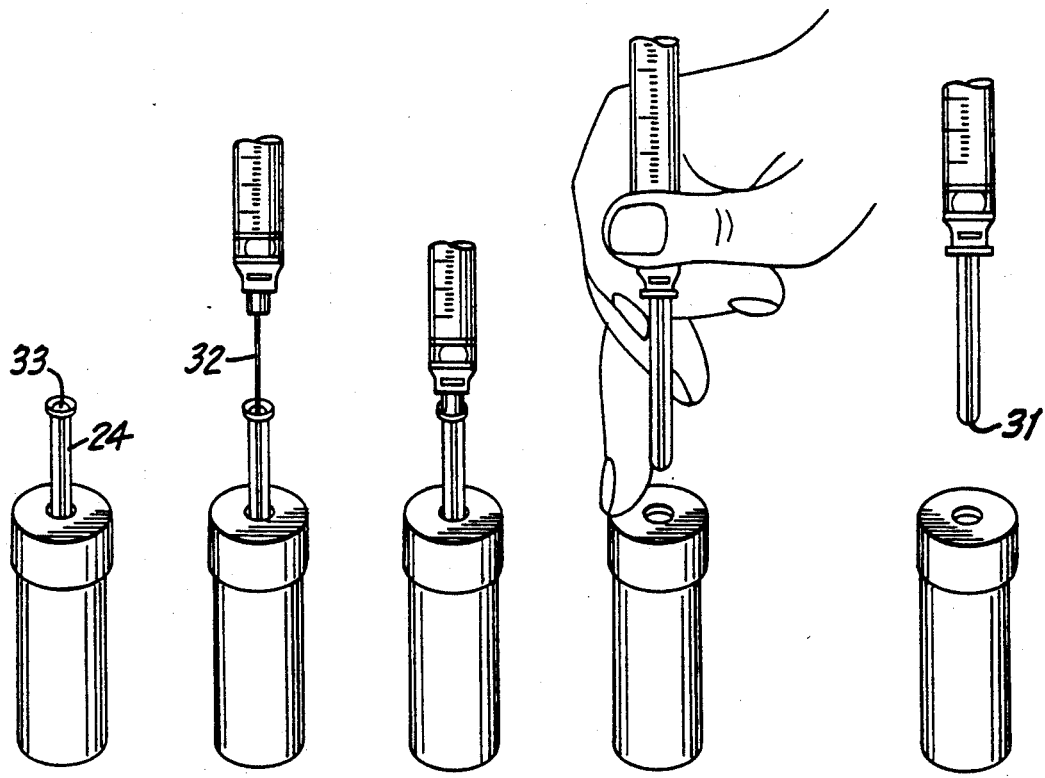
FIG. 3a   FIG. 3b   FIG. 3c   FIG. 3d   FIG. 3e

METHOD AND APPARATUS FOR ENABLING SAFE RECAPPING OF HYPODERMIC NEEDLES

This is a continuation of co-pending application Ser. No. 07/546,181 filed on Jun. 28, 1990, now abandoned.

BACKGROUND AND OBJECTS OF THE INVENTION

The present invention relates generally to devices which facilitate bedside infection control in hospitals or any type of medical facility by temporarily safeguarding used hypodermic needles immediately after use, until they can be properly disposed of, and, more particularly, to a one-handed recapping device and like devices for safely enabling reinsertion of a used needle into its original packing sheath.

With the widespread use of disposable medical implements, particularly hypodermic needles, a definite need has developed for ways to safely and conveniently handle and transport such implements after use, so that disposal can be effected without risk of exposing any person handling the used implements to injury, infection or disease by puncture or contact with a used needle or syringe. The tragic outbreak of the highly contagious AIDS disease has dramatically heightened the need for safer handling, storage and disposal of such implements.

In today's medical facilities, a wide variety of disposable needle and syringe devices are routinely used to administer medication by injection and intravenous ("I.V.") procedures, and for intravenous blood collection. Once an injection is given, a blood sample drawn, or an I.V. needle removed from a patient, both the needle and/or syringe used in the procedure may be contaminated and must be disposed of in a safe manner. The problem is particularly heightened because competent medical personnel will not leave a patient unattended immediately after administering an I.V. procedure in order to search out disposal facilities for the used hypodermic needle. Consequently, while the nurse or physician is attending to the patient, unsheathed contaminated needles have been momentarily placed on bedside tables, the used needles have been placed on the patient's bedding, and bed mattresses have even been used as a type of "pincushion" to temporarily hold the contaminated needle.

Once it had been common practice to break or cut the needle after use and before transport to ultimate disposal so as to eliminate the sharp end point, thereby reducing the risk of puncture, scratching or other injury which might result from handling. However, the very act of breaking or cutting the needles gives rise to a substantial danger that accidental puncture might occur during the breaking or cutting operations, thus exposing the holder to possible injury and, further, to possible infection or disease as a result of such puncture. In addition, residual medication or blood in the needle or the syringe can splatter onto the person or his clothes, and, potentially harmful fumes from the residual medication could be inhaled as a result of the so-called aerosol effect. Furthermore, the blades of the cutting tool are now recognized as a breeding ground for germs, bacteria and other disease-causing micro-organisms to which an unsuspecting person cutting the needle could be unnecessarily exposed.

Recently, an even greater danger has been recognized in connection with the handling and disposal of used needles as well as other sharp medical implements. It is now recognized that certain diseases, most notably Hepatitis B, can be transmitted by covert percutaneous—i.e., by merely contacting the contaminated needle or implement.

While the used needle portion of a hypodermic needle/syringe combination presents the most significant risk of injury or infection through accidental puncture or scratching of a person's skin, the used syringe part may also present a risk of infection. For example, a used syringe can contain residual blood or medication which, if exposed to a person's skin, may be absorbed topically (particularly if a cut or break in the skin is present) and may cause a serious internal infection or other reaction.

As a result of the foregoing dangers, it is preferred current practice to dispose of such devices intact, without dismantling them. One contemplated solution lies in disposing of the whole, used hypodermic needle/syringe by recapping it before disposal with its original, protective sheath. The contaminated needle point and shaft would thus be isolated against inadvertent contact or puncture until it could be deposited in a disposal unit. Previously, the recapping solution was discouraged because of the inherent risk of accidental puncture if the person was unsuccessful in re-inserting the needle into the sheath. Very recently, however, the Occupational Safety and Health Administration ("OSHA") OSHA has stated that needle recapping is permissible so long as some type of recapping device is utilized to aid in the recapping procedure.

One proposal for a recapping device requires the device to be held in one hand (with the sheath held in the device) while the needle is held in the other hand for insertion into the sheath. While such a device may be effective in reducing the risk of accidental needle sticks, it suffers a significant drawback because it requires two hands to use. Once a user picks up the handle portion with one hand, the handle is unsterile by any contaminant on the user's hand. When someone else picks up the device, his/her hand is immediately contaminated by any residue from the previous user's hand.

Accordingly, it is an object of the present invention to provide a new and improved device to aid in recapping a used needle. It is a more specific object of the invention to provide a new and improved recapping device which permits one-handed recapping for safely recapping a hypodermic needle immediately after use.

It is also an object of the present invention to provide a one-handed recapping device for conveniently and safely recapping a hypodermic needle immediately after use in its original sheath prior to the needle's ultimate disposal without exposing the person handling the device to the risk of injury, infection or disease by puncture of contact with the used needle or syringe.

It is a further object of the present invention to provide a conveniently sized and easily transportable one-handed needle recapping device for conveniently and safely recapping, at the point of use, a used needle/syringe assembly prior to ultimate disposal.

A still further object of the present invention is to provide a one-hand operable needle recapping device for safely recapping used hypodermic needles, in their original sheaths, at the point of use, that may also be used with external holders or other receptacles conveniently placed for ensuring ready access to the device.

It is still a further object of the present invention to provide a needle recapping device for hypodermic syringes that is free standing and self supporting so as to enable medical personnel to recap used hypodermic needles with the use of only one hand.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a recapping device for hypodermic needles that is self supporting and includes support means for vertically supporting a sheath or the like so that the needle may be recapped in its original sheath by using only one hand. Generally, the recapping device includes a housing member having an opening at its top end and resilient gripper means for securely grasping a needle sheath yet allowing easy release of the sheath when desired, e.g., after recapping is completed. A weight or other form of ballast is provided at the bottom end of the housing to maintain the recapping device upright while the recapping operation is performed.

A sheath engaging shoulder is fixed within the housing, generally below the resilient gripper means of the housing. The engaging shoulder preferably is cone-shaped to engage the closed end of the needle's sheath, thereby providing support for the sheath when the needle is re-inserted therein.

The resilient sheath gripping means has an opening generally disposed coaxially along the longitudinal axis of the housing. The opening is preferably smaller in diameter than the smallest contemplated sheath, so that as the sheath is inserted through the opening, the resilient gripper will exert a holding force onto the sheath so as to maintain the sheath upright for recapping yet will permit release when desired.

Additionally, the resilient gripper can accommodate different sized (diameter) sheaths. The gripper may be formed from a strip of foam folded into, preferably, a generally triangular configuration. Advantageously, a number of clips (preferably two) are attached to the strip at the folds to conveniently form a generally triangular-shaped opening that provides effective holding ability with all sizes of sheaths. An end cap, having an opening generally disposed coaxially with the longitudinal axis of the housing, fits snugly over the open top end of the housing. The cap is removable, allowing access to the sheath supporting device and the gripper. The cap's opening may be frusto-conical in shape to serve as a convenient guide for the sheath.

In another embodiment of the invention, the use may select the amount or quantity of ballast incorporated into the housing, according to need or desire. Here, the housing is open at both end. A dividing wall separates the housing into top and bottom chambers. In place of a sheath engaging element, an indentation, preferably conical in shape but not necessarily so limited, is formed in the dividing wall the indentation being substantially coaxial with the longitudinal axis of the housing.

The bottom chamber of the housing is filled with a desired quantity of ballast. The quantity of ballast is easily added to or subtracted from by using granular or other forms of weight that provide a convenient way to selectively determine the quantity of ballast. Of course, putties, compounds, or other forms of easily alterable weight could also be used. A closed but removable cap fits snugly over the bottom end of the housing so as to keep the ballast within the chamber.

A further embodiment provides no ballast. Thus, the housing can be made short, providing even more convenience and flexibility in transporting the recapping device about the person. Support for the device is safely provided by placing a free finger onto the top cap of the recapping device only after the needle has been re-inserted into its protective sheath. Of course, a free finger on the hand holding the hypodermic needle should be employed to lessen the possibility of injury to the free hand. The pressure exerted by the free finger discourages the recapping device from lifting when the recapped needle is removed from the recapping device. This finger touching method is simple, natural, and provides an effective way to operate the recapping device.

The various embodiments may be provided with means for securing the recapping device to various surfaces or to the person. They may be provided with clips, so that the recapping device may be clipped onto a shirt pocket or belt for ease of transport and rapid access while in use. A suction cup can also be provided at the bottom of the recapping device, particularly convenient where additional support for the device is desired or needed (for example, where the recapping device might be subjected to slippery conditions).

A holder for supporting the device might also be provided. The holder may be mounted at the bedside of the patient, to a hospital cart, or at any other place providing ready access to the recapping device. Adhesive backing or other varied means can be provided to conveniently secure the holder in various locations.

A locking mechanism can be provided to hold the recapping device securely within the holder, lest the recapping device be accidentally jarred out of the holder. Conveniently, stock appenditures on the housing of the recapping device may serve to engage/disengage the recapping device from the holder. Thus, a standard recapping device may be used both in a stand-alone manner or in conjunction with the holder.

Alternatively, the invention may be mounted in a beaker-like container, such as a bottle, or a spherical bubble. Here, the recapping device may not necessarily include ballast, as the container may provide a sufficiently wide base to prevent the recapping device from tipping over during use. However, the base of the container itself may be provided with ballast or suction cups to provide additional support.

The container may be opaque or transparent. The container may be filled with liquids and/or weighted objects. The container may be decorated with faces or other designs. Thus, in addition to serving its intended purpose, the invention may serve as a welcome distraction to alleviate the fears that children (or adults, for that matter) suffer at the sight of a hypodermic needle.

BRIEF DESCRIPTION OF DRAWINGS

The invention will be described in greater detail by way of reference to the following drawings, in which:

FIG. 1 is a side elevation view of one embodiment of the present invention;

FIG. 2 is a cross-sectional view of the embodiment of FIG. 1 as seen along line 2-2;

FIGS. 3a-3e are a sequential depiction of one-handed recapping of a hypodermic needle according to the invention;

DETAILED DESCRIPTION OF THE DRAWINGS

Figure 4:
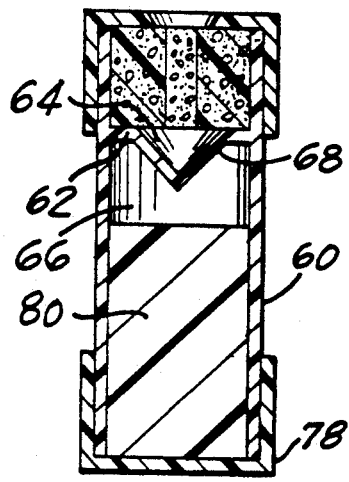
FIG. 4 is a cross-sectional view, similar to FIG. 2, of a modified embodiment of the present invention.

Referring now to the accompanying drawings, wherein like reference characters refer to like parts throughout the various views, there is illustrated in FIGS. 1 and 2 one embodiment of the hypodermic needle recapping device according to the present invention. Generally, the recapping device 10 is of a convenient size and shape so that it may be easily carried on the person of medical personnel or sit inconspicuously on a medcart or a patient bed table, etc. As herein shown, the recapping device 10 includes a tubular cylindrical housing 12, but other shapes may be substituted.

As shown, the housing 12 may have a bottom wall 14, side walls 16, and an open top end 18. An end cap 20, having an opening 22 substantially coaxial with the longitudinal axis of housing 12, may be designed to fit snugly over housing 12 around side walls 16 so as to substantially enclose open end 18 (except for opening 22).

Opening 22 is proportioned to allow a hypodermic needle sheath 24 to be inserted part-way into the recapping device 10. The opening 22 is thus preferably formed sufficiently wide to accommodate the largest sized sheath 24 contemplated for use with the device. Top cap 20 can be removable so as to permit access to the interior of housing 12, the benefit of which will become apparent hereafter.

It will be appreciated that the bottom wall 14 may be deleted from housing 12 so as to form an open end at the bottom housing 12. In this case, a bottom cap (not shown) similar to top cap 20, but not having an opening, may be used in place of bottom wall 14 to contain the contents of housing 12 while providing access thereto.

Advantageously, a weight or ballast 26 is disposed generally at the bottom of housing 12 for stability during use. Ballast 26 may comprise any convenient weighty material, such as plaster of paris, lead, or various forms of hardenable compound. Ballast 26 serves to maintain and support recapping device 10 in an upright position, particularly during the recapping operation. Accordingly, the quantity and density of ballast 26 may be selected so as to render recapping device 10 self-standing, taking into consideration the typical forces to which the recapping device 10 will be subjected during the recapping operation.

Within the interior of housing 12 a sheath support 28 is fixedly disposed, preferably substantially coaxial with the longitudinal axis of housing 12. As shown by FIG. 2, support 28 may be arranged so as to be rigidly supported by the ballast material 26. The support 28 may, for example, have the configuration of a golf tee, which advantageously permits the manufacturer to easily adjust the height and orientation of support 28 with respect to the open top end 18 of housing 12. Alternatively, as explained with reference to FIGS. 4 et seq., the support device 28 need not encompass a separate element but can be made as an integral part of housing 12.

As preferably embodied, support 28 includes a recessed, conically shaped support portion 30 that serves to engage the bottom end of hypodermic needle sheath 24. As herein shown, support portion 30 has a conical shape, thereby permitting cap 20 to accommodate various widths of sheath 24. The recapping device 10 is thus rendered extremely versatile, because differently-sized needles will constantly be encountered by the user of the invention.

Support portion 30 is preferably positioned in vertical relation to the open end 18 of housing 12 to receive a sufficient length of the sheath 24 (e.g., 20% -50%) so that the sheath is steadily supported during the recapping procedure. Thus, as illustrated in FIGS. 2, 3a and 3b, sheath 24 is supported so as to permit its open end 33 to remain exposed above top cap 20. The sheath's open end 33 remains easily accessible to hypodermic needle 32, preventing the possibility of needle pricks or other injury that might occur if open end 33 were not readily visible to the user of the invention. Simultaneously, a sufficient length of sheath 24 remains embedded within housing 12 for snugly holding the sheath and preventing it from tipping over or sliding about during the operation.

A support collar 36 may be snugly inserted above ballast 26 and around the portion of support 28 above the ballast to ensure the support does not break if subjected to too much force. This support collar 36 can be made from a material that can include rubber, styrofoam, or other material that easily adapts to the shape of housing 12 so as to provide secure lateral support for support 28.

As preferably embodied, recapper 10 includes sheath gripper means (indicated generally at 38). Sheath gripper 38 can be formed from a resilient material such as rubber, plastic foam or sponge-like material, or crosslink polyethylene or other material with a memory. The sheath gripper 38 is disposed above support portion 30.

Sheath gripper 38 includes an opening 40 that is substantially coaxial with the longitudinal axis of housing 12 and opening 22 in end cap 20. The opening 40 is preferably centered above the trough in support portion 30. When gripper 38 is in its relaxed state, the opening 40 can be substantially narrower in width than the smallest sheath 24 contemplated for use with the invention. By virtue of its resilient nature, gripper 38, and its opening 40, will expand upon the entry of sheath 24, thereby applying a snug gripping force to sheath 24. Additionally, since opening 40 is expandable, gripper 38 can accommodate sheaths of varying widths or shapes, rendering recapping device 10 extremely versatile.

As seen in FIG. 2, gripper 38 generally fills the space between top cap 20 and support portion 30. Gripper 38 is thus prevented from dislodging from housing 12 when sheath 24 is removed from the device. Moreover, since top cap 20 can be made removable, the gripper 38 may be easily accessed for removal or replacement. This is of significant benefit since ideally the recapping device 10 is designed for long term use and gripper 38 may suffer decreased resiliency, become worn, or otherwise require replacement during prolonged use of the device.

Operation of the invention is illustrated in FIGS. 3a-3c. When a needle is to be used, the sheath is removed, as usual, and inserted into housing 12 through the opening 22 in top cap 20. (Opening 22 may have a slight frusto-conical shape to help guide closed end 31 of sheath 24 through the opening 22.) The sheath then passes through opening 40 in gripper 38 until it engages support portion 30. This enables the user to quickly insert sheath 24 into the recapping device, a significant consideration where attending personnel are busily engaged and predominantly concentrating on the needs of the patient.

After the injection has been administered, the needle point is simply re-inserted into the open end (33) of the sheath until fully received back in the sheath as it was when in its sterile condition (FIG. 3c). The needle, now solidly enclosed within the sheath is removed from device 10 (with the aid of a finger as shown in FIG. 3d) and has been rendered safe to handle until it can be deposited in a proper disposal device.

Figure 6A:
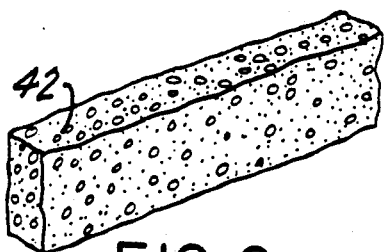
FIGS. 6a-6c show the formation of one embodiment of the sheath gripper of the present invention.
Figure 6C:
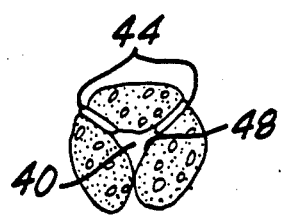
Figure 6B:
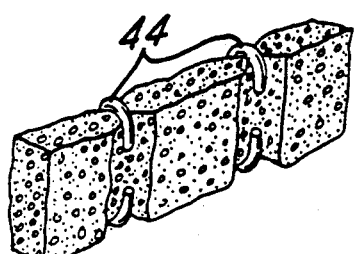

The sheath gripper 38 may be configured or formed in a number of ways. One embodiment is represented by FIGS. 6a-6c. A strip or section 42 of resilient material, preferably rectangular in cross-section but not necessarily so limited, is folded twice to form a generally triangular opening 40. To this end, clips 44 may be fastened to the strip along the fold lines to help form the opening. The strip 42 is then folded about clips 44 to form the triangular-shaped opening 40. The opening 40 is preferably formed so that when the sheath gripper 38 is placed within housing 12 the opening will be substantially co-axial with the longitudinal axis of housing 12. It has been found that the opening 40 formed by this "clip and fold" method provides particularly effective holding ability for all sized sheaths 24. This, in part, is believed to be due to the relatively vertical sheath engaging walls 48 that result from the method.

Referring to FIG. 2, the recapping device 10 may also be provided with a clip 50, attached to the exterior surface of housing 12, that provides a relatively convenient way to transport recapping device 10 about the person. The clip 50 may have an end 52 elastically fixed to housing 12. A free end 54 permits a shirt pocket, belt, or other support element to enter the gap 56 formed by the outside surface of housing 12 and the clip 50. Advantageously, the free end 54 of clip 50 may be upturned or may be provided with a raised nub or other appenditure (not shown), explained hereafter.

Referring to FIG. 4, another embodiment of a recapping device according to the invention includes the sheath support as an integral part of the housing. As here embodied, dividing wall 62 separates housing 60 into a top chamber 64 and a bottom chamber 66. A depression 68, preferably conical in shape but not necessarily so limited is formed in the dividing wall to provide the support portion for a sheath. The sheath gripper and top cap are substantially identical to those described above with reference to FIGS. 1, 2 and 6a-6c.

As shown in FIG. 4, the bottom end of housing 60 is preferably open to enable fabrication by simple two-part injection molding. A bottom cap 78 is provided to close off the bottom of the housing. Bottom cap 78, which provides a snug fit with the bottom end of housing 60, is preferably removable to provide access to ballast 80. This advantageously allows ballast 80 to be removed or replaced according to need or desire. By forming an integral wall 62 in housing 60, it will be found that the ballast 80 may fill part or all of the lower housing member.

Figure 4A:
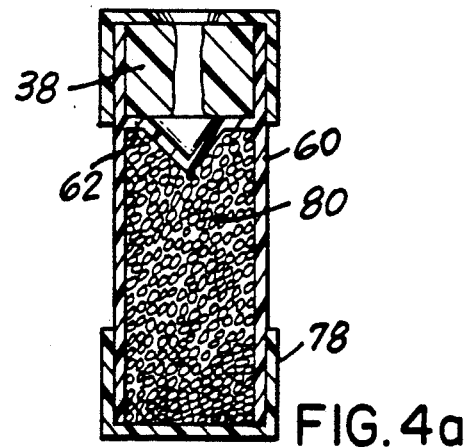
FIG. 4a is a similar cross-sectional view of a further modified version of the embodiment shown in FIG. 4.

Referring them to FIG. 4a, ballast can include two or more separate pieces of weighted material or a quantity of weighted "shot" material, thereby allowing the user of the recapping device to properly select the quantity of ballast needed or desired.

Figure 5A:
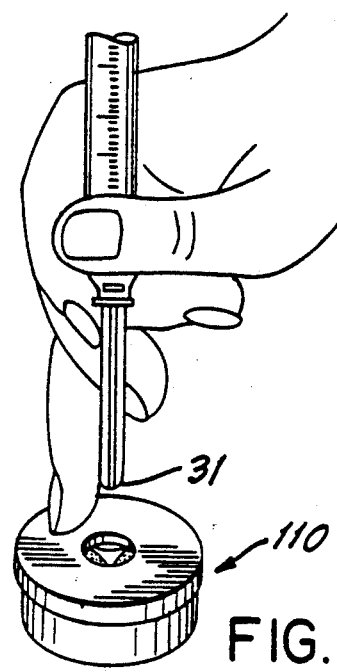
FIGS. 5a, 5b and 5c represent top perspective, top, and side cross-sectional views, respectively, of another embodiment of the present invention.
Figure 5B:
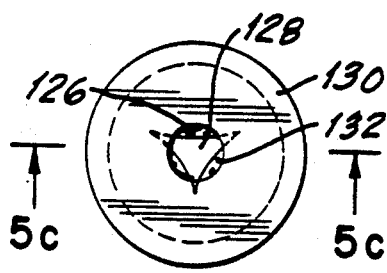
Figure 5C:
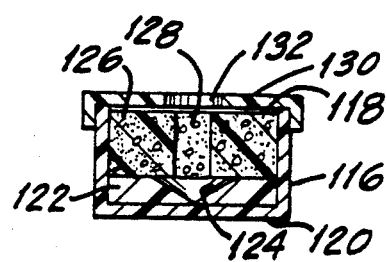

A further embodiment of a recapping device (110) according to the invention is illustrated in FIGS. 5(a-)-5(c). Here, the recapping device (110) can be effectively miniaturized by eliminating ballast material. This provides additional convenience in transporting the recapping device, the device conveniently slipping into a shirt or pants pocket. As illustrated, the recapping device (110) includes a significantly shorter housing 116 as compared with the foregoing embodiments. Housing 116 has an open end 118 and a closed end 120. A sheath engaging insert 122, having a conical indentation 124 substantially coaxial with the longitudinal axis of housing 116, serves to engage the closed end 31 of sheath 24, substantially as described above.

A sheath gripper 126, provided with an opening 128 as previously described, rests on the surface of sheath engaging insert 122. The sheath gripper 126 may be formed by the clip and fold method illustrated in FIGS. 6a-6c, but may be of less height than the foregoing embodiments. The recapping device 110 is also provided with a top cap 130, having an opening 132 as previously described. The opening 132 may have a frusto-conical shape that serves to guide sheath 24 into engagement with the indentation 124 of sheath engaging insert 122, substantially as previously described.

Figure 11:
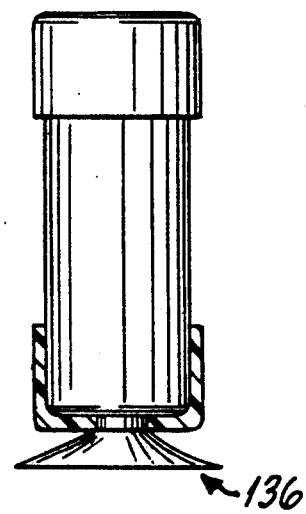
FIG. 11 illustrates a suction-cup mounting arrangement.

In addition to the ballast means herein described for the various embodiments, other types of support are contemplated for use with the invention. For example, FIG. 11 illustrates a suction cup 136 placed at the base of the recapping device, providing an additional way to ensure the stability and upright position of the recapping device. This is significant when, for example, the recapping device might be placed on slippery surfaces (such as in an emergency or operating room, where blood or other bodily fluids might be present), or where the recapping device might be subjected to sudden jostling (particularly prevalent in moving vehicles such as ambulances).

Figure 8:
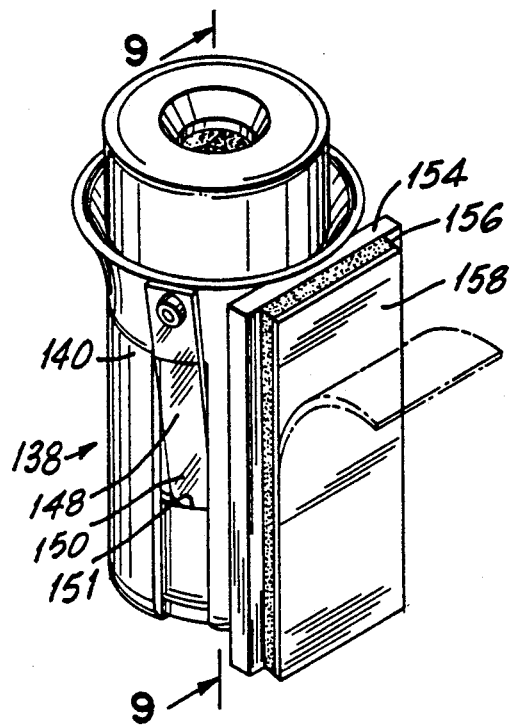
FIG. 8 is a perspective view illustrating a recapping device according to the present invention in a holder having surface mounting capability.
Figure 9:
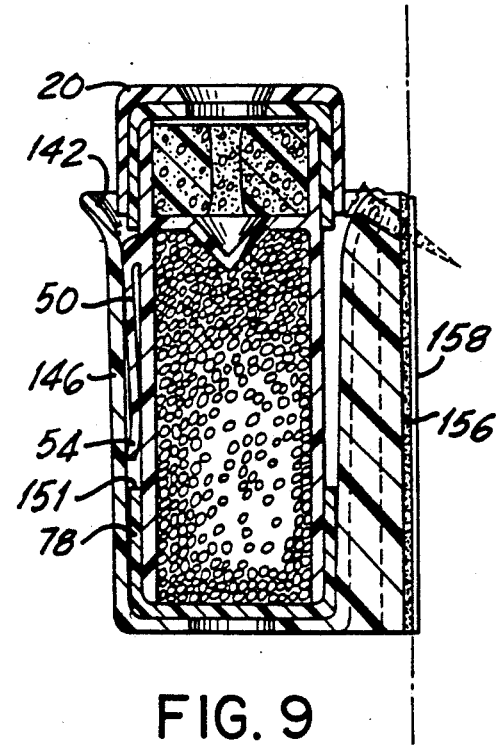
FIG. 9 is a cross-sectional view of the embodiment depicted in FIG. 8 as seen along line 9—9.
Figure 10:
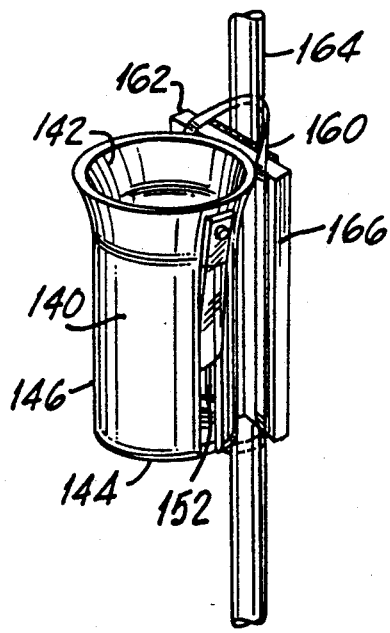
FIG. 10 is a perspective view illustrating the pole-mounting capability of an embodiment according to the present invention.

In FIGS. 8-10, a recapping device holder 138 is shown for use with the embodiments previously described. The holder 138, may be mounted at the bedside of the patient, to medical utility carts, or in any number of areas, by an adhesive backing (FIG. 8). Alternatively, it may be mounted to a vertical pole such as supports an intravenous device (FIG. 10).

Holder 138 includes a hollow housing 140 that is sufficiently wide to permit entry of the of the previously described embodiments of recapping devices. Hollow housing 140, having an open top end 142, a closed bottom end 144, and sidewalls 146, is preferably shorter than the recapping device to allow easy access to the opening provided in the top cap of the recapping device.

In order to prevent the recapping device from accidentally dislodging from holder 138, a biased retaining clip 148 may be provided. The retaining clip 148 is mounted to the sidewall of holder 138, with its distal end 150 protruding into the interior of the holder 138 through a slotted opening 152 in the sidewall 146. When the device is inserted into the holder, the bottom end cap of the recapping device pushes clip 148 outwardly until it rests at the bottom of holder 138. Thereupon, the distal end 150 of retaining clip 148 "snaps" behind the upper edge of lip 151 of the bottom cap so as to prevent withdrawal of the recapping device.

Figure 7:
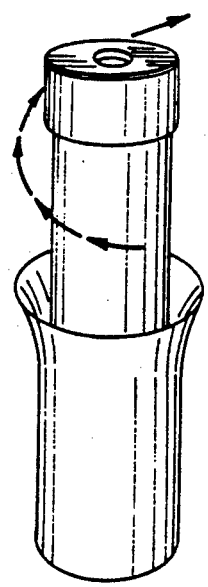
FIG. 7 illustrates the twisting removal of an embodiment of the present invention from its associated holder.

The clip 50 provided on the housing of the recapping device serves to disengage the recapping device from holder 138 when desired. By twisting the recapping device (see FIG. 7), the upturned end 54 of the recapping device clip 50 comes into engagement with and slides beneath retaining clip 148, forcing the retaining clip 148 outwardly through slot 152 and allowing withdrawal of the recapping device.

Holder 138 can be provided with a mounting wall 154, having a relatively flat engaging surface 156, that allows easy mounting of the holder 138 to most surfaces. For example, screws or bolts (not shown) may be drilled through the plate 154 so that engaging surface 156 comes to rest against a wall or other vertical surface. Similarly, suction cups (not shown) can also be provided on the surface 156.

Advantageously, an adhesive backing 158 may be provided on the engaging surface 156 so that holder 138 can be easily mounted without additional parts or the use tools.

Where it is desired to mount the holder to a rounded surface such as a pole (for example, the leg of a medical cart or intravenous support pole), the supporting force provided by adhesive backing 158 can be supplemented with additional pressure from an elastic element 160, such as a rubber band. In use, the elastic element 160 is first slipped into engagement about a side edge 162 of plate 154. Next, the element 160 is stretched around the rear of pole 164 and slipped into engagement about the opposing side edge 166 of plate 154. Elastic 160 exerts pressure onto the rounded surface of pole 164, forcing adhesive backing 158 to securely adhere thereto.

Figure 12:
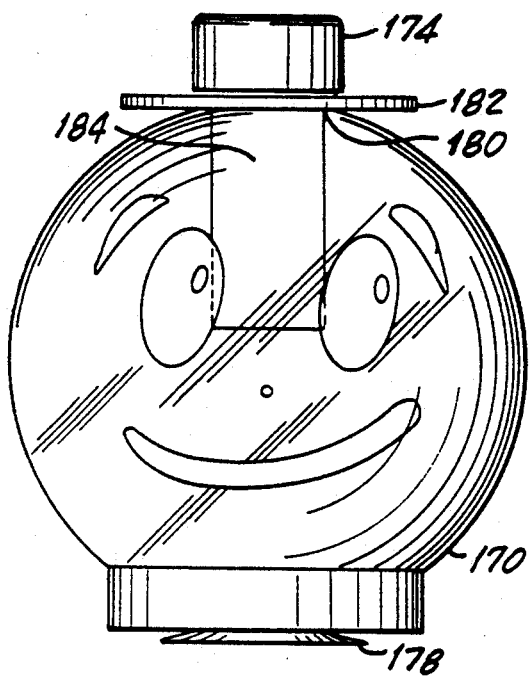
FIG. 12 illustrates a container mounting arrangement for the present invention.
Figure 13:
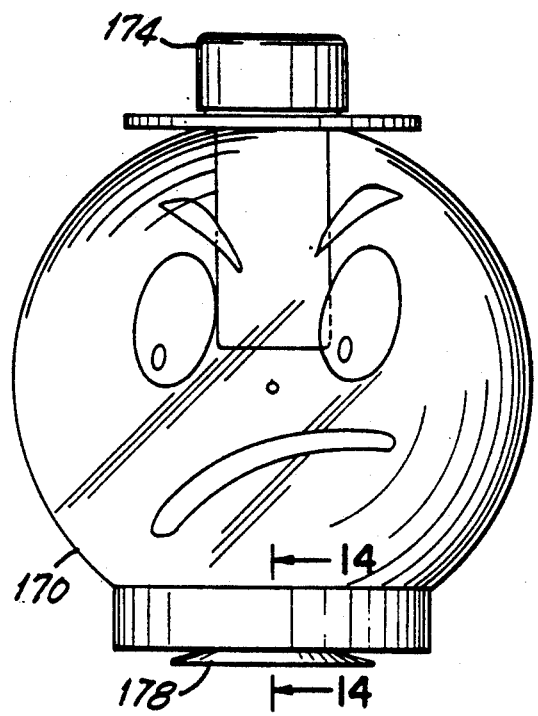
FIG. 13 is another view of the embodiment of FIG. 12 as seen in a different direction.
Figure 14:
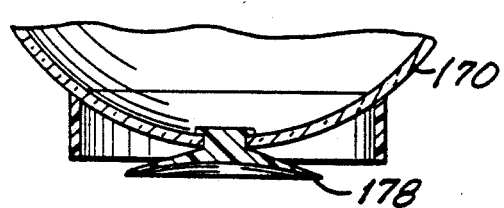
FIG. 14 illustrates the suction-cup mounting arrangement of the embodiment of FIG. 13 as seen along line 14—14.
Figure 15:
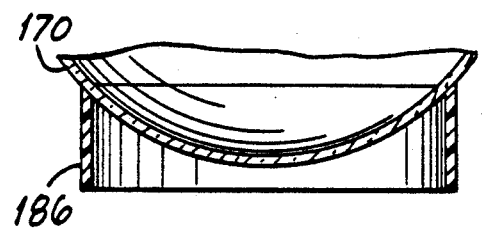
FIG. 15 illustrates a ring mounting arrangement for the embodiment of FIGS. 12-13 of the present invention.
Figure 16:
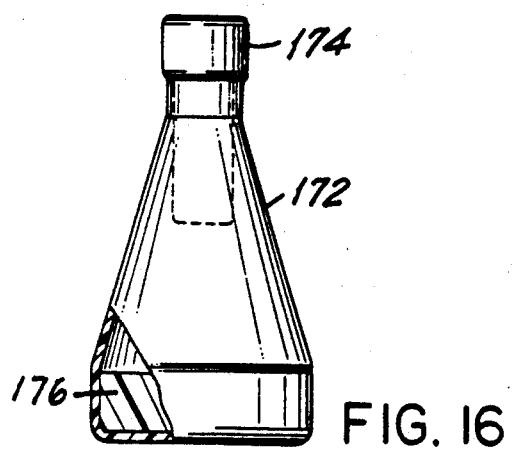
FIG. 16 shows another container mounting arrangement for the present invention.

Additionally, the recapping device according to the invention may be mounted in a supporting container. As seen in FIGS. 12, 13 and 16, the recapping device is mounted in supporting containers 170 and 172 so that top cap 174 remains exposed to a hypodermic needle to be recapped. The base of containers 170 and 172 may be provided with ballast 176 or suction cups 178 to provide additional stability to recapping device. The wide base of containers 170, 172 enable the recapping device to enjoy added upright stability.

A particularly interesting variation of the recapping device according to the invention is seen in FIGS. 12 and 13. Here, the mounting container 170 is spherical in shape, providing a ready medium for embellishing the recapping device with designs, especially with faces or similar decoration possessing anthropomorphic qualities. This advantageously serves to remove the perhaps "sterile" feeling associated with medical instruments. It is also especially useful in alleviating the fears individuals display at the sight of hypodermic needles, the designs or faces providing the patient with a welcome distraction.

Here, the recapping device is supported through an opening 180 in sphere 170 by a wide supporting lip 182 which surrounds the housing 184. The sphere 170 may include a supporting collar 186 having a flat bottom, which enables the sphere 170 to rest on a flat surface without wobbling. A suction cup 178 may also be provided to ensure added stability.

The sphere can be made opaque or clear. It can be filled with liquids, colored sand, or with other objects only limited by one's imagination. As illustrated, the sphere 170 has been designed with a "smiling" face on one side and a "frowning" face on the other. Thus, the sphere 170 can provide a means to convey the "mood" of the patient or that of the attending medical personnel. The device thereby serves as an avenue allowing attending medical personnel to interact with the patients, especially with children.

It will be apparent that other and further forms of the invention may be devised without departing from the spirit and scope of the appended claims, it being understood that this invention is not limited to the specific embodiment shown.

What is claimed is:

1. A recapping device to assist in recapping the needle of a hypodermic needle/syringe by a one-handed operation, comprising:
   a housing having top and bottom ends, said housing having at least its top end open;
   a ballast material generally at the bottom end of said housing for stabilizing said recapping device in an upright position; and
   a sheath gripper disposed in said housing for releasably supporting a needle sheath, said sheath gripper formed from a strip of a resilient material such as rubber or foam and folded about a plurality of fold lines so as to form an expandable, roughly triangularly shaped sheath supporting opening for resiliently supporting said needle sheath in an upright position in such a way that a used needle can be recapped by re-inserting the needle tip into the sheath held by said recapping device yet said gripper allows withdrawal of the sheath once reattached to the needle.

2. The recapping device of claim 1, further comprising a clip resiliently fixed at one end along the outside surface of said housing, said clip disposed so that a gap exists between the outside surface of said housing and the inside surface of said clip said clip having a free end with an upturned portion.

3. The recapping device of claim 1, further comprising a cap secured to the open end of said housing, said cap disposed above said sheath gripping means to prevent said sheath gripping means from dislodging from said housing, said cap provided with an opening substantially coaxial with the opening in said gripping means.

4. The recapping device of claim 3, wherein the opening in said cap has a frusto-conical shape serving to guide said sheath through the opening and into engagement with said gripper.

5. The recapping device of claim 1, wherein said opening of said sheath gripper is resiliently expandable to accommodate different sized sheaths.

6. A recapping device according to claim 5, wherein said sheath gripper further includes a clip member at each fold line to help define said fold line.

7. A recapping device which enables a needle to be re-inserted in a sheath or like protective sleeve by a one-handed recapping operation, said device comprising:
a housing having a hollow interior and divided into top and bottom chambers by a dividing wall, said housing having open top and bottom ends, said wall having an indentation generally coaxial with the longitudinal axis of said housing for engaging an end of said sheath;
a ballast material placed in the bottom chamber of said housing for maintaining said recapping device in an upright position;
a cap secured to the bottom end of said housing for retaining said ballast material within said housing;
a sheath gripper provided in the top chamber of said housing and disposed above said dividing wall defining an expandable, roughly triangularly shaped opening substantially coaxial with the longitudinal axis of said housing for gripping and supporting said sheath in an upright position, said sheath gripper formed from a strip of resilient material which is folded about a plurality of fold lines so as to define said roughly triangular opening; and
a cap secured to the top end of said housing, said cap disposed above said sheath gripper to prevent said sheath gripper from dislodging from said housing, said top cap having an opening substantially coaxial with the longitudinal axis of said housing.

8. The recapping device of claim 7, wherein said recapping device further comprises a clip resiliently fixed at one end along the outside surface of said housing, said clip having an upturned free end.

9. The recapping device of claim 7, wherein said roughly triangular opening in said sheath gripper is formed by folding said strip of resilient material along said fold lines that are defined by multiple clips placed along the length of said strip, said strip folded about said clips so as to form said roughly triangular opening substantially coaxial with the longitudinal axis of said housing.

10. The recapping device of claim 7, wherein the opening of said top cap is frusto-conical in shape, said shape serving as a guide for directing said sheath through said opening in said sheath gripper and into engagement with said hollow indentation of said dividing wall.

11. The recapping device of claim 7, wherein the quantity of said ballast means is user selectable.

12. The recapping device of claim 11, wherein said ballast material comprises two or more pieces of ballast material.

13. The recapping device of claim 12, wherein said ballast means comprises buckshot.

14. A recapping device which enables a needle to be re-inserted in a sheath or like protective sleeve by a one-handed operation, said device comprising:
a rigid housing having a hollow interior and divided into top and bottom chambers by a dividing wall, said housing having open top and bottom ends, said wall having a hollowed indentation substantially coaxial with the longitudinal axis of said housing for engaging an end of said sheath;
a ballast material placed in the bottom chamber of said housing for maintaining said recapping device in an upright position;
a cap secured to the bottom end of said housing for retaining said ballast means within said housing;
a sheath gripper provided in the top chamber of said housing and disposed above said dividing wall and defining an expandable roughly triangularly shaped opening substantially coaxial with the longitudinal axis of said housing for gripping and supporting said sheath in an upright position, said sheath gripper formed from a strip of resilient material which is folded about a plurality of fold lines to define said expandable opening;
a cap secured to the top end of said housing, said cap disposed above said sheath gripper to prevent said sheath gripper from dislodging from said housing and having an opening substantially coaxial with the longitudinal axis of said housing;
a clip resiliently fixed at one end of the exterior of said housing, said clip having an upturned end opposing said fixed end; and
a holder for releasably containing said recapping device in an upright position, said recapping device secured and released by said holder by appendages integral to said recapping device.

15. The recapping device of claim 14, wherein said triangular opening in said sheath gripper is formed by folding said strip of resilient material about said fold line that are defined by a plurality of clip members disposed along the length of said strip.

16. The recapping device of claim 14, wherein said holder further comprises unitary means for releasing and retaining said recapping device, said releasing and retaining means cooperating with said integral appendages of said recapping device.

17. The recapping device of claim 16, wherein said means for retaining and releasing said recapping device from said holder comprises a resilient clip, said clip resiliently attached to the top end of said holder, said clip engaging the bottom cap of said recapping device through an opening in said holder, said clip disengaged from said bottom cap when said resilient clip is engaged by an appendage of said recapper.

18. The recapping device of claim 17, wherein said appendage comprises said clip fixed to the exterior of said housing.

19. The recapping device of claim 14, wherein said holder further comprises means for securing said holder to non-horizontal surfaces.

20. The recapping device of claim 19, wherein said means for securing said holder comprises a rigid plate having an engaging surface tangential to said holder, said plate secured to said non-horizontal surfaces via fixation means.

21. The recapping device of claim 20, wherein said fixation means comprises an adhesive layer disposed on said outside surface of said rigid plate.

22. The recapping device of claim 21, wherein said fixation means further comprises an elastic element for pressing said adhesive layer into engagement with said non-horizontal surface.

23. The recapping device of claim 20, wherein said fixation means comprises screws threadably engaged through said plate into engagement with said non-horizontal surface.

24. A recapping device which enables a needle to be re-inserted in a sheath or like protective sleeve by a one handed operation, comprising:
 a rigid housing having top and bottom ends, said housing having at least one open end;
 a sheath gripper provided at the top of said housing formed from a resilient strip and folded about a plurality of clips disposed along the length of said strip to form a resilient expandable, roughly triangularly shaped opening for gripping and supporting said sheath in an upright position;
 a removable cap secured to the top end of said housing, said removable cap disposed above said sheath gripper to prevent said sheath gripper from dislodging from said housing, said removable cap having an opening substantially co-axial with the longitudinal axis of said housing, such that a used needle can be recapped by inserting the needle into the opening of said sheath gripper which can thereafter be withdrawn from said recapping device once re-attached to said needle.

25. The recapping device of claim 24, wherein said device is supported within a sphere, said sphere having support means for supporting said sphere on horizontal surfaces.

26. The recapping device of claim 26, wherein said support means comprises a cylindrical ring.

27. The recapping device of claim 26, wherein said support means comprises a suction cup.

28. The recapping device of claim 26, wherein said sphere has been decorated.

29. A method of recapping a needle with one hand, comprising steps of:
 a. releasably supporting a vertical sheath by a recapping device having a sheath gripper formed from a resilient material strip folded about a plurality of fold lines disposed along the length of said strip to form roughly a triangular shaped expandable sheath gripping opening;
 b. inserting said needle into the open end of said sheath until said sheath is securely attached to said needle; and
 c. withdrawing the needle and sheath from the recapping device.

30. The recapping method of claim 29, further comprising the step of applying pressure to the recapping device with a finger on the hand grasping the needle during the withdrawal of the needle and sheath from the recapping device.

* * * * *